United States Patent [19]
Magee

[11] 4,069,342
[45] Jan. 17, 1978

[54] METHOD FOR REGULATING RESTS USING ALKYLTHIOTRICHLORODICYANOBENZENES

[75] Inventor: Thomas A. Magee, Mentor, Ohio

[73] Assignee: Diamond Shamrock Corporation, Cleveland, Ohio

[21] Appl. No.: 519,343

[22] Filed: Oct. 30, 1974

Related U.S. Application Data

[63] Continuation-in-part of Ser. No. 423,937, Dec. 12, 1973, abandoned.

[51] Int. Cl.$^2$ .................... A01N 9/12; A01N 9/14; C07C 121/54
[52] U.S. Cl. .................... 424/304; 260/454; 260/456 R; 260/465 D; 260/465 E; 260/465 F; 260/465 G; 424/302; 424/303
[58] Field of Search ............ 260/465 G; 424/304, 424/302, 303

[56] References Cited
U.S. PATENT DOCUMENTS

| | | | |
|---|---|---|---|
| 2,919,225 | 12/1959 | Heininger et al. | 260/465 X |
| 3,290,353 | 12/1966 | Battershell et al. | 260/465 |
| 3,901,935 | 8/1975 | Domenico | 260/465 G |

OTHER PUBLICATIONS

Carter et al., J.C.S. Perkin II, pp. 2104–2107 (1972).

*Primary Examiner*—Dolph H. Torrence
*Attorney, Agent, or Firm*—Helen P. Brush

[57] ABSTRACT

Novel compounds useful for the control of pests such as fungi and bacteria have the formula

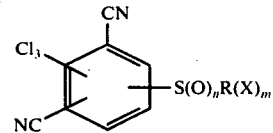

wherein $n$ is 0, 1 or 2; R is a $C_{1-12}$ alkylene; $C_{2-12}$ alkenylene; $C_{2-12}$ alkynylene; arylene or aralkylene radical; X is hydrogen, halogen, alkoxy, acyl, acyloxy, alkylthio, alkylsulfonyl, cyano, thiocyanato, alkylsulfonyloxy or amino group; and $m$ is 1–3, inclusive; with the proviso that when $n$ is 0, the -CN groups are in the 1- and 3-positions and X is hydrogen, R is not a methylene radical.

2 Claims, No Drawings

METHOD FOR REGULATING RESTS USING ALKYLTHIOTRICHLORODICYANOBENZENES

BACKGROUND OF THE INVENTION

This application is a continuation-in-part of my copending application, Ser. No. 423,937, filed Dec. 12, 1973, and now abandoned.

Field of the Invention

This invention relates to organic compounds useful as pesticides and, more particularly, to certain organosulfur derivatives of tetrachlorodicyanobenzenes having fungicidal and bactericidal properties.

Description of the Prior Art

The compound, 2,4,5-trichloro-6-(methylthio)-benzene-1,3-dicarbonitrile, is disclosed in J.C.S., Perkin Trans. II, 2104 (1972). The crystalline structure of the compound which may also be designated as 4-methylthio-2,5,6-trichloroisophthalonitrile is described in Acta. Cryst., Section B, 28 (Pt. 11), 3430–4 (1972). No biological activity or other utility is reported for this material in these references.

SUMMARY OF THE INVENTION

The novel organosulfur derivatives of tetrachlorodicyanobenzenes of this invention may be represented by the formula

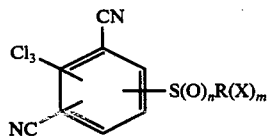

wherein $n$ is 0, 1 or 2; R is a $C_1-_{12}$ alkylene; $C_2-_2$ alkenylene; $C_2-_{12}$ alkynylene; arylene or aralkylene radical; X is hydrogen, halogen, alkoxy, acyl, acyloxy, alkylthio, alkylsulfonyl, cyano, thiocyanato, alkylsulfonyloxy or amino group; and $m$ is 1–3, inclusive; with the proviso that when $n$ is 0, the -CN groups are in the 1- and 3-positions and X is hydrogen, R is not a methylene radical.

Compounds of the invention wherein $n$ of the above formula is 0 are biologically active and also are useful as intermediates in the preparation of the organosulfinyl- and organosulfonyltrichlorodicyanobenzene compounds of the invention. The aforesaid known 4-methylthio-2,5,6-trichloroisophthalonitrile likewise has been found to be pesticidally active.

DESCRIPTION OF THE PREFERRED EMBODIMENTS

It is to be understood that the dicyanobenzene compounds of this invention may be designated more specifically as alkylthio-, alkylsulfinyl- or alkylsulfonyl derivatives of either tetrachlorophthalonitrile, tetrachloroisophthalonitrile or tetrachloroterephthalonitrile, depending upon whether the cyano (CN) substituents of the benzene ring are in the ortho-, meta-, or para-position with respect to each other. Accordingly, this more specific terminology generally will be used hereinafter to designate individual compounds of the invention. These compounds, of course, still can be broadly designated as organosulfur derivatives of tetrachlorodicyanobenzenes.

Because of their desirable properties and comparative ease of manufacture, certain compounds of the invention are presently preferred. These particular compounds conform to the formula

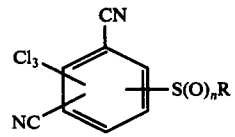

wherein $n$ is 0, 1 or 2; and R is a methyl or ethyl radical, with the proviso that when $n$ is 0 and the —CN groups are in the 1- and 3-positions, R is not methyl.

Accordingly, specific reference may be made hereinafter to these particular compounds. Such specific reference, however, is not intended to limit the invention in any way, but to merely serve as specific illustration thereof.

As specific organosulfonyltrichlorodicyanobenzenes, i.e., those compounds which conform to the structure

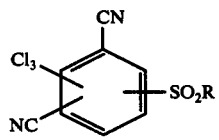

wherein R is a methyl or ethyl group, there may be mentioned:
 4-methylsulfonyl-2,5,6-trichloroisophthalonitrile
 3-(and/or 4)-methylsulfonyltrichlorophthalonitrile
 2-ethylsulfonyl-3,5,6-trichloroterephthalonitrile
 4-ethylsulfonyl-2,5,6-trichloroisophthalonitrile
 3-(and/or 4)-ethylsulfonyltrichlorophthalonitrile
 2-methylsulfonyl-3,5,6-trichloroterephthalonitrile.

Specific organosulfinyltrichlorodicyanobenzenes conforming to the structure

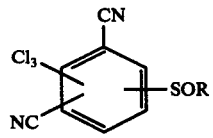

wherein R is a methyl or ethyl group, encompassed herein include:
 4-methylsulfinyl-2,5,6-trichloroisophthalonitrile
 3-(and/or 4)-methylsulfinyltrichlorophthalonitrile
 2-ethylsulfinyl-3,5,6-trichloroterephthalonitrile
 4-ethylsulfinyl-2,5,6-trichloroisophthalonitrile
 3-(and/or 4)-ethylsulfinyltrichlorophthalonitrile
 2-methylsulfinyl-3,5,6-trichloroterephthalonitrile.

As specific novel organothiotrichlorodicyanobenzenes, i.e., those compounds which conform to the structure

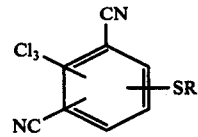

wherein R is methyl or ethyl, with the proviso that when the —CN groups are in the 1- and 3-positions, R is not methyl, there may be mentioned:

4-ethylthio-2,5,6-trichloroisophthalonitrile
3-(and/or 4)-ethylthiotrichlorophthalonitrile
2-methylthio-3,5,6-trichloroterephthalonitrile
2-ethylthio-3,5,6-trichloroterephthalonitrile
3-(and/or 4)-methylthiotrichlorophthalonitrile.

The organothiotrichlorodicyanobenzene intermediates are themselves prepared by reacting approximately equimolar proportions of an appropriate mercaptotrichlorodicyanobenzene and an alkylating agent such as dialkyl sulfate in an alkaline aqueous medium. The dialkyl sulfate is added to the dicyanobenzene reactant in small portions over a period of several minutes as this reaction is highly exothermic in nature and difficult to control. After the addition of the alkylating agent, the reaction is carried to completion by heating the reaction mixture at an elevated temperature, e.g., on a steam bath, for a time period of 1 to 4 hours. The reaction mixture is then cooled and filtered. The crude solids isolated are washed with water. The product is obtained by selective extraction of the crude solids and recrystallization from suitable solvents.

The organothiotrichlorodicyanobenzene compounds are all colored solid materials. They normally are less than 5 percent soluble in water, while being greater than 5 percent soluble in common organic solvents.

The organosulfinyl- and organosulfonyltrichlorodicyanobenzene compounds of the invention are conveniently prepared from the appropriate aforesaid organothiotrichlorodicyanobenzenes prepared according to the above-described procedure by reacting the intermediate with a peroxy compound in an acid medium such as a per acid, e.g., peracetic acid, or with hydrogen peroxide in an acid medium such as acetic acid. Generally, from about 0.1 to 10 moles of the peroxy compound may be suitably reacted for each mole of the sulfide compound. Within this range, the peroxy compound and the appropriate organothiotrichlorodicyanobenzene are preferably reacted in approximately equimolar proportions to assure optimum yields of an organosulfinyl derivative. A molar ratio of about 2.0 to 3.5 of the peroxy compound per mole of organothiotrichlorodicyanobenzene is employed to assure complete oxidation of the sulfide to the corresponding organosulfonyl derivative. The reaction typically is carried out at temperatures ranging generally from about 5° C to about 50° C, preferably from about 30° C to 50° C when preparing an organosulfinyl derivative. Temperatures of 50°–110° C, optimally ranging from 80° C to 105° C are employed when preparing an organosulfonyl derivative. Under these conditions, reaction times generally are 2–5 hours.

Upon completion of the reaction, the solid product is obtained by first pouring the reaction mixture into an ice-water bath and then isolating the solid which precipitates. The crude product typically is washed well with hot alkanol, e.g., isopropanol, and finally dried.

The novel compounds of this invention and the known 4-methylthio-2,5,6-trichloroisophthalonitrile are all effective pesticidal compounds. Although they may be applied in undiluted form to the plant or other material to be protected, it is usually desirable to apply these compound in admixture with either solid or liquid inert, pesticidal adjuvants. For example, the compounds can be applied to plants for pesticidal purposes by spraying the plants with aqueous or organic solvent dispersions of the compounds. Choice of an appropriate solvent is determined by factors such as concentration of active ingredient, the volatility required in the solvent, cost of the solvent, and nature of the material being treated.

Solvents, which can be employed as carriers for these compounds, include hydrocarbons such as benzene, toluene, xylene, kerosene, diesel oil, fuel oil, hydrocarbons, and naphthas; ketones such as acetone, methyl ethyl ketone, and cyclohexanone; chlorinated hydrocarbons such as trichloroethylene, perchloroethylene; esters such as ethyl acetate, amyl acetate and butyl acetate; monoalkyl ethers of ethylene and diethylene glycols such as the monomethyl and monoalkyl ethers, the monoethyl ether of propylene glycol; alcohols such as ethanol, isopropanol, pentanols, and the like.

These compounds can also be applied to plants and other materials in conjunction with inert solid adjuvants or carriers such as talc, attapulgite, chalk, diatomaceous earth, koalinite, montmorillonite, pyrophyllite, and other silicates, silica, lime, calcium carbonate, certain organic carriers such as walnut shell flour, wood flour, ground corn cobs, and the like.

It is often desirable to use a surfactant (a surface active agent) in pesticidal compositions. An anionic, nonionic or cationic surfactant can be used in the formulation of either solid or liquid compositions. Typical surfactants include alkyl sulfonates, alkylaryl sulfonates, alkyl sulfates, alkylamide sulfonates, alkylaryl polyether alcohols, fatty acid esters of polyhydric alcohols, ethylene oxide addition products of these esters; ethylene oxide addition products of long-chain mercaptans, and the like.

For dusting purposes, formulations preferably are employed in which the active ingredient is present in an amount of 5 to 50% of the total weight. However, concentrations outside this range are operative and compositions containing from 1 to 99% of active ingredient, by weight, are contemplated wherein the remainder is carrier and/or any other desired additive or adjuvant.

For spray application, the active ingredient may be dissolved or dispersed in a liquid carrier, such as water or other suitable liquid. The active ingredient can be added in the form of a solution, suspension, dispersion or emulsion in aqueous or nonaqueous medium. Desirably, 0.5 to 1.0% by weight of surfactant is present in the liquid composition.

For adjuvant purposes, any desired quantity of surfactant may be employed, such as up to 250% by weight of the active ingredient. If the surfactant is used only to impart wetting qualities to a spray solution, as little as 0.05% or less by weight of the surfactant need be used. Larger quantities of surfactant are used because of biological behavior of the surfactant rather than its wetting properties. These considerations are particularly important in the treatment of plants. The active ingredient in liquid formulations often may not be more than 30% by weight of the total and may be 10% by weight or even as low as 0.01% by weight.

The terms "pesticide" and "pesticidal" are used herein are intended to refer to the killing and/or control of fungi, bacteria and other microorganisms. It will be appreciated that applications commonly referred to as bactericidal and fungicidal are contemplated by these terms.

For a fuller understanding of the nature and objects of this invention, reference may be made to the following examples which are given to illustrate the invention and are not to be construed in a limiting sense. The infrared spectrum for each product described herein is consistent with the assigned structure. All percentages, proportions, and quantities given in these examples are by weight unless otherwise indicated. Likewise all references to temperature are as ° C unless otherwise indicated.

EXAMPLES 1-7 6

Preparation of 4-Methylthio-2,5,6-trichloroisophthalonitrile

To a stirred slurry of 25.8 g (0.098 M) of 4-mercapto-2,5,6-trichloroisophthalonitrile in 50 ml of water containing 4.4 g (0.11 M) of sodium hydroxide is added 12.6 g (0.1 M) of dimethyl sulfate slowly. The temperature of the reaction mixture increases to about 70° C. The mixture is then heated at 90°-100° C for one hour, cooled and filtered to isolate the crude product as a light tan solid. The crude product is washed with water, dried and recrystallized from a benzene-petroleum ether mixture to obtain 13.6 g (50% yield) of a yellow solid. This product which melts at 157°-159° C is identified as 4-methylthio-2,5,6-trichloroisophthalonitrile.

Table 1 gives the following data on this known compound as well as novel alkylthiotrichlorodicyanobenzenes prepared by this procedure employing either dimethyl sulfate or diethyl sulfate as the alkylating agent. The reaction temperature ranges typically from 50° to 80° C. The table lists the reaction time, % yield and melting point of product (° C), and elemental analytical data as % C, H, and N.

EXAMPLES 7-12

Preparation of 4-Ethylsulfonyl-2,5,6-trichloroisophthalonitrile

A slurry is prepared of 15.5 g (0.053 M) of 4-ethylthio-2,5,6-trichloroisophthalonitile (Product of Example 2) in 100 ml of glacial acetic acid. To this slurry is added 22.7 g (0.2 M) of 30% aqueous hydrogen peroxide, and the resulting mixture is heated at 105°-108° C for 2.5 hours. After cooling, the reaction mixture is poured onto ice and water. The precipitate which forms is isolated by filtration. It is then slurried in methanol, refiltered and air dried to yield 13.8 g (80% yield) of a pale yellow solid. This material melts at 237°-38° C and is identified as 4-ethylsulfonyl-2,5,6-trichloroisophthalonitrile by elemental analysis.

Table 2 below gives data for this compound as well as for other organosulfonyltrichlorodicyanobenzenes of this invention which are prepared by the same procedure employing appropriate organothiotrichlorodicyanobenzene intermediates (Products of Examples 1 and 3-6). Included in the table are the reaction temperature and time for each reaction, the % yield, and the melting point (° C) for each product, and elemental analytical data as % C, H, and N.

TABLE 1

| Example | Product | Reaction Time hrs | Yield % | Melting Point ° C | Analysis Calculated % | | Found % | |
|---|---|---|---|---|---|---|---|---|
| 1 | 4-methylthio-2,5,6-tri-chloroisophthalonitrile | 1.0 | 50 | 157-9 | C H N | 38.9 1.1 10.1 | C H N | 39.35 1.2 9.95 |
| 2 | 4-ethylthio-2,5,6-tri-chloroisophthalonitrile | 1.5 | 47 | 151-2 | C H N | 41.2 1.7 9.6 | C H N | 41.4 1.8 9.6 |
| 3 | 2-methylthio-3,5,6-tri-chloroterephthalonitrile | 1.5 | 51 | 153-5 | C H N | 38.9 1.1 10.1 | C H N | 39.7 1.3 10.2 |
| 4 | 3-(and/or 4)-methylthio-trichlorophthalonitrile | 2.0 | 66 | 116-8 | C H N | 38.9 1.1 10.1 | C H N | 39.1 1.2 10.0 |
| 5 | 3-(and/or 4)-ethylthio-trichlorophthalonitrile | 2.0 | 63 | 96-8 | C H N | 41.4 1.7 9.6 | C H N | 41.2 1.8 10.1 |
| 6 | 2-ethylthio-3,5,6-tri-chloroterephthalonitrile | 1.25 | 90$^a$ | 165-8 | C H N | 41.2 1.7 9.6 | C H N | 41.3 1.9 9.5 |

$^a$Crude product yield.

TABLE 2

| Example | Product | Reaction Temp. — ° C | Reaction Time — hrs | % Yield | Melting Point ° C | Analysis Calculated % | | Found % | |
|---|---|---|---|---|---|---|---|---|---|
| 7 | 4-ethylsulfonyl-2,5,6-trichloro-isophthalonitrile | 105-8 | 2.5 | 80 | 237-8 | C H N | 37.1 1.6 8.7 | C H N | 37.4 1.6 9.0 |
| 8 | 4-methylsulfonyl-2,5,6-trichloro-isophthalonitrile | 100 | 4.0 | 91$^a$ | 269-70 | C H N | 34.9 1.0 9.1 | C H N | 35.3 1.1 9.5 |
| 9 | 2-methylsulfonyl-3,5,6-trichloro-terephthalonitrile | 105-8 | 3.0 | 76 | 253-5 | C H N | 34.9 1.0 9.1 | C H N | 35.2 1.1 9.3 |
| 10 | 2-ethylsulfonyl-3,5,6-trichloro-terephthalonitrile | 100 | 2.5 | 64 | 221-2 | C H N | 37.1 1.6 8.7 | C H N | 37.7 1.6 9.0 |
| 11 | 3-(and/or 4)-methylsulfonyltri-chlorophthalonitrile | 105-8 | 2.5 | 49 | 159-61 | C H N | 34.9 1.0 9.1 | C H N | 35.1 1.1 9.2 |
| 12 | 3-(and/or 4)-ethylsulfonyltri-chlorophthalonitrile | 100 | 3.5 | 62 | 166-8 | C H N | 37.1 1.6 8.7 | C H N | 37.2 1.5 9.0 |

$^a$Crude product yield.

EXAMPLES 13-16

Preparation of 3-(and/or 4)-ethylsulfinyltrichlorophthalonitrile

A stirred mixture of 19.2 g (0.066 M) of 3-(and/or 4)-ethylthiotrichlorophthalonitrile (product of Example 5), 12.5 g (0.066 M) of 40% peracetic acid, and 110 ml of acetic acid is heated at 40°-47° C for three hours. The cooled reaction mixture is treated with 125 ml of water. The resulting solids are filtered off and dried to yield 20.4 g (100% yield) of product which is determined to be 3-(and/or 4)-ethylsulfinyltrichlorphthalonitrile by infrared and NMR spectra and by elemental analysis of % C, H, and N.

Table 3 below gives data for this compound as well as other representative organosulfinyltrichlorodicyanobenzene compounds of this invention which are prepared by the same procedure employing appropriate organothiotrichlorodicyanobenzene intermediates (Products of Examples 1, 3, and 6).

TABLE 3

| Example | Product | % Yield | Melting Point °C | Analysis | Calculated % | Found % |
|---|---|---|---|---|---|---|
| 13 | 3-(and/or 4)-ethylsulfinyl-trichlorophthalonitrile | 100 | 165-6 | C | 39.0 | 39.7 |
|  |  |  |  | H | 1.6 | 1.9 |
|  |  |  |  | N | 9.4 | 8.9 |
| 14 | 4-methylsulfinyl-2,5,6-trichloroisophthalonitrile | 94 | 226-31 | C | 36.8 | 37.8 |
|  |  |  |  | H | 1.0 | 1.5 |
|  |  |  |  | N | 9.5 | 9.5 |
| 15 | 2-methylsulfinyl-3,5,6-trichloroterephthalonitrile | 77 | 223-4 | C | 36.8 | 36.7 |
|  |  |  |  | H | 1.0 | 1.2 |
|  |  |  |  | N | 9.5 | 10.1 |
| 16 | 2-ethylsulfinyl-3,5,6-trichloroterephthalonitrile | 84 | 167-70 | C | 39.0 | 39.8 |
|  |  |  |  | H | 1.6 | 1.6 |
|  |  |  |  | N | 9.1 | 9.1 |

EXAMPLE 17

Early Blight Test (EB) and Late Blight Test (LB)

The early blight test (EB) determines the ability of the test compound to control early blight, *Alternaria solani* (Ell. and Mart.) Jones and Grant incited leaf spotting symptoms, on laminae of *Lycopersicon esculentum*, tomato var. Bonny Best, and the late blight test (LB) the ability to control late blight. *Phytophthora infestans* (Mont.) deBary incited leaf spotting symptoms on laminae of *Lycopersicon esculentum*, tomato var. Bonny Best.

A basic formulation is prepared containing 0.125 g of the test compound (or 0.125 ml if a liquid), 4.0 ml stock emulsifier solution (0.25% Triton X-155, Rohm and Haas Co., Philadelphia, Pa., in acetone by volume) and 96.0 ml deionized water. Concentration of the test compound in this formulation is 1250 ppm . Lower concentrations of the test compound are obtained by dilution of the basic formulation with stock emulsifier solution containing 4 ml of the emulsifier in 96.0 ml deionized water. The lower concentrations differ only in test compound content.

Formulations of the test compound prepared by the above procedure are sprayed on single tomato transplants having 3 to 5 expanded leaves. When the spray deposit dries (about 1 hour after spraying), the tomato plants are mass inoculated in the early blight test by spraying with a conidial suspension (about 2.0 × 10⁴ per ml) of A. solani is deionized water fortified with 1% frozen commercial orange juice and in the late blight test by spraying with a sporangial suspension (about 1.5 × 10⁵ per ml) of P. infestans in deionized water. Uniform suspension delivery is standardized at 20 ml/0.5 min.

Inoculated plants are immediately placed in a water saturated atmosphere at 70° F in the early blight test and at 60° F in the late blight test. The plants then are incubated under these conditions for 24 hours. At the end of the incubation period, the test plants are removed to greenhouse culture. In the early blight test, total lesion count on the three youngest, fully expanded leaves on each plant is made 48 hours after removal from the incubator and in the late blight test, total lesion count on the three youngest, fully expanded leaves on each is made 72 hours after removal from the incubator. The % disease control is then calculated using the total lesion count from the treated plants and the untreated control plants and the results rated using the following scale:

| Rating | 90% Control at the Indicated Concentration in ppm |
|---|---|
| 2 | >64 |
| 3 | 32-64 |
| 4 | 16-32 |
| 5 | 8-16 |

Using this proceudre, results obtained with the test compounds are as follows:

TABLE 4

| Test Compound | Disease Control Rating | |
|---|---|---|
| Product of Example | EB | LB |
| 1 | 4 | 4 |
| 2 | 4 | 2 |
| 3 | 2 | 3 |
| 4 | 3 | 2 |
| 5 | 2 | 2 |
| 6 | 2 | 2 |
| 7 | 4 | 2 |
| 8 | 2 | 2 |
| 9 | 3 | 4 |
| 10 | 5 | 5 |
| 11 | 4 | 3 |
| 12 | 3 | 2 |

EXAMPLE 18

Brown Spot Test (BS)

This test determines the potential chemical activity of the test compound to control brown spot (BS), *Helminthosporium oryzae* van Breda, incited leaf spotting symptoms, on laminae of oryza sativa L., rice var. Nato.

Formulations of the test compounds are prepared as described in Example 17 and are applied as spray treatments on rice plants 10-14 days after seeding. The plants are mass inoculated by spraying with a conidial suspension (about 4.0 × 10⁴ per ml) of the organism in deionized water containing surfactant. The suspension is delivered at a rate of 20 ml/ 0.5 min.

The inoculated plants are immediately placed in a water-saturated atmosphere at 70° F and incubated for 24 hours. The plants are then removed to the greenhouse and the incidence of brown spots on the leaves is visually estimated 1 day after incubation. The % disease control is calculated from these visual estimates compared to the brown spot incidence on untreated control plants. The results obtained, rated using the scale given in Example 17, are as follows:

TABLE 5

| Test Compound Product of Example | Disease Control Rating Brown Spot (BS) |
| --- | --- |
| 1 | 5 |
| 3 | 2 |
| 4 | 2 |
| 5 | 2 |
| 8 | 4 |
| 10 | 5 |
| 11 | 3 |
| 12 | 2 |

EXAMPLE 19

Bean Rust Protectant (BR) Test

The bean rust protectant (BR) test determines the ability of the test compound to protect beans from *Uromyces phaseoli* (Pers.) Wint. uredospore incited disease symptoms, pustules.

Formulations of the test compounds prepared by the procedure described in Example 17 are applied as a foliage spray on three seeded bean plants var. Pinto having unifoliolate leaves 75% expanded in a pot having a soil surface area of 9.0 in.$^2$.

After the test chemical is applied as a foliage spray, the plants are dried and then mass introduced with a uredospore suspension (about $4.0 \times 10^5$ per ml) of *U. phaseoli* in deionized water containing 5 ppm of Tween 20 surfactant. Uniform uredospore suspension delivery is standardized at 20 ml/0.5 min.

Inoculated test plants are incubated in a water saturated atmosphere at 60° to 70° F for 24 hours. After incubation, test plants are removed to greenhouse culture. A visual estimate of rust pustule incidence is made 10 to 14 days after incubation. The percent disease control is then calculated using the estimates of rust pustule incidence on treated and untreated test plants and the results rated using the following scale:

| Rating | 90% Control at the Indicated Concentration in ppm |
| --- | --- |
| A | >300 |
| B | 150–300 |
| C | 75–150 |
| D | 37.5–75 |
| E | 18.8–37.5 |
| F | 9.4–18.8 |
| G | 4.7–9.4 |

Using this procedure, results are as follows:

TABLE 6

| Test Compound Product of Example | Disease Control Rating |
| --- | --- |
| 1 | F |
| 2 | F |
| 3 | D |
| 4 | D |
| 5 | B |
| 6 | B |
| 8 | E |

TABLE 6-continued

| Test Compound Product of Example | Disease Control Rating |
| --- | --- |
| 9 | D |
| 10 | E |
| 11 | B |

EXAMPLE 20

Corn Rust Protectant (CR) Test

This test determines the ability of the test compound to protect corn, var. Golden X Bantam from corn rust incited by the fungus *Puccinia sorghi* Schw.

Formulations of the test compounds are prepared as described in Example 17. Each test formulation is applied as a foliage spray onto three seedling corn plants, each having three leaves, in a pot having a soil surface area of 9.0 in.$^2$.

After application of the test formulation, the plants are dried and mass inoculated as described in Example 19, employing a ureodospore suspension of the test fungus. The inoculated plants are stored in a saturated atmosphere at 70° F for 24 hours. They are then removed to a greenhouse and a visual estimation of rust pustule incidence on the foliage is made 10 to 14 days after storage in the greenhouse. The percent disease control is calculated using the estimates of rust pustule incidence on treated and untreated test plants and these results are rated using the scale given in Example 19, with the following ratings obtained:

TABLE 7

| Test Compound Product of Example | Disease Control Rating |
| --- | --- |
| 1 | G |
| 2 | G |
| 3 | D |
| 4 | E |
| 5 | B |
| 8 | G |
| 9 | D |

EXAMPLE 21

Bactericide Test

This test determines the potential chemical activity of the test compounds to control bacterial incitants of animal diseases at various concentrations.

Formulations of the test compounds are prepared as described in Example 17. For each test, a single 100 × 15 mm polystyrene Petri dish is plated with a mixture of 8 ml of 2% agar (Difco Bacto) plus 0.8% nutrient broth, 0.2% tryptic broth (Difco) and 2.0 ml of the test formulation.

The agar surface is simultaneously inoculated with cell suspensions from cultures of each of the following animal pathogens:

(Hg) *Haemophilus gallinarum* Delaplane, Erwin and Stuart; (Sa) *Staphylococcus aureus* Rosenbach; (Sf) *Streptococcus faecalis* Andrews and Horder; and (Sg) *Salmonella gallinarum* (Klein) Bergey.

After inoculation, the plate is incubated for 48 hours at 28° ±2° C. Inhibition of organism growth is rated visually by comparison with the organism growth on nontreated control agar. Each compound is rated for bacterial control using the following rating scale:

| Rating | 100% Control at the Indicated Concentration in ppm |
|---|---|
| 1 | 32–64 |
| 2 | 16–32 |
| 3 | 8–16 |
| 4 | 4–8 |
| 5 | 2–4 |

Control ratings obtained with the test compounds are shown in Table 8.

TABLE 8

| Test Compound Product of Example | Bactericide Tests Bacterial Growth Control Rating | | | |
|---|---|---|---|---|
| | Hg | Sa | Sf | Sg |
| 1 | 5 | | | |
| 7 | | 1 | | |
| 8 | 2 | 2 | | |
| 9 | | | 2 | |
| 10 | | 1 | 1 | |
| 11 | | | 1 | |
| 12 | | | 3 | |

It is to be understood that although the invention has been described with specific reference to particular embodiments thereof, it is not to be so limited since changes and alterations therein may be made which are within the full intended scope of this invention as defined in the appended claims.

I claim:

1. A method for regulating pests selected from the group consisting of bacteria and fungi which comprises contacting the pest environment with a pesticidally-effective amount of a compound of the formula

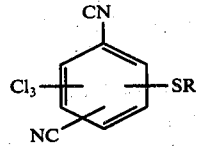

wherein R is methyl or ethyl.

2. The method of claim 1 wherein the pesticidal compound is
4-methylthio-2,5,6-trichloroisophthalonitrile,
4-ethylthio-2,5,6-trichloroisophthalonitrile,
2-methylthio-b 3,5,6-trichloroterephthalonitrile,
3- or 4-methylthiotrichlorophthalonitrile,
2-ethylthio-3,5,6-trichloroterephthalonitrile, or
3- or 4-ethylthiotrichlorophthalonitrile.